US011304654B2

(12) United States Patent
Shin et al.

(10) Patent No.: US 11,304,654 B2
(45) Date of Patent: Apr. 19, 2022

(54) METHOD FOR DETECTING ABNORMAL RESPIRATION USING A PHOTOPLETHYSMOGRAPHY (PPG) SIGNAL

(71) Applicant: ELECTRONICS AND TELECOMMUNICATIONS RESEARCH INSTITUTE, Daejeon-si (KR)

(72) Inventors: Hyun Soon Shin, Daejeon (KR); Chan Young Hahm, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 636 days.

(21) Appl. No.: 15/696,428

(22) Filed: Sep. 6, 2017

(65) Prior Publication Data

US 2018/0103896 A1  Apr. 19, 2018

(30) Foreign Application Priority Data

Oct. 18, 2016  (KR) ........................ 10-2016-0135222

(51) Int. Cl.
*A61B 5/00* (2006.01)
*A61B 5/08* (2006.01)
(Continued)

(52) U.S. Cl.
CPC .......... *A61B 5/4818* (2013.01); *A61B 5/0004* (2013.01); *A61B 5/0205* (2013.01);
(Continued)

(58) Field of Classification Search
CPC . A61B 5/4818; A61B 5/02416; A61B 5/0004; A61B 5/0205; A61B 5/0826
See application file for complete search history.

(56) References Cited

U.S. PATENT DOCUMENTS

2010/0076321 A1* 3/2010 Zhang ................... A61B 5/686
600/483
2010/0152560 A1   6/2010 Turcott
(Continued)

FOREIGN PATENT DOCUMENTS

JP        2014/530057 A     11/2014
KR    10-2011-0088138 A      8/2011
(Continued)

OTHER PUBLICATIONS

KIPO Office Action, dated Nov. 30, 2018, for Korean Patent Application No. 10-2016-0135222 which corresponds to the above-identified U.S. application.

*Primary Examiner* — Serkan Akar
*Assistant Examiner* — Aminah Asghar
(74) *Attorney, Agent, or Firm* — LRK Patent Law Firm

(57) ABSTRACT

An abnormal respiration detection apparatus includes a sensor for sensing a PPG signal from an optical signal reflected and received from a user's body; a band pass filter for extracting a signal of a required band from the PPG signal; an analog-to-digital converter for performing a digital conversion on the filtered PPG signal; and an abnormal respiration recognition unit deriving a respiration rate signal from the digital-converted PPG signal, deriving a plurality of respiration rate characteristic values through a time axis analysis on the derived respiration rate signal, and detecting an abnormal respiration using the derived plurality of respiration rate characteristic values. The embodiments can be utilized to monitor the survival of elders who live alone, soldiers isolated in a military operation, persons isolated in disaster and accident sites, thereby contributing to public and social safety and building of welfare society and nation.

3 Claims, 6 Drawing Sheets

(51) Int. Cl.
*A61B 5/0205* (2006.01)
*A61B 5/024* (2006.01)

(52) U.S. Cl.
CPC ........ *A61B 5/02416* (2013.01); *A61B 5/0816* (2013.01); *A61B 5/6824* (2013.01); *A61B 5/0826* (2013.01); *A61B 5/725* (2013.01); *A61B 5/7225* (2013.01); *A61B 5/7278* (2013.01); *A61B 5/742* (2013.01)

(56) References Cited

U.S. PATENT DOCUMENTS

| | | | |
|---|---|---|---|
| 2011/0054341 A1 | 3/2011 | Jeong et al. | |
| 2011/0112442 A1* | 5/2011 | Meger | A61B 5/4094 600/595 |
| 2012/0283581 A1* | 11/2012 | Olde | A61B 5/0816 600/485 |
| 2013/0144182 A1 | 6/2013 | Jeong et al. | |
| 2014/0128697 A1* | 5/2014 | Parfenova | A61B 5/02007 600/328 |
| 2014/0316226 A1* | 10/2014 | Ferber | A61B 5/0205 600/315 |
| 2015/0164375 A1* | 6/2015 | Schindhelm | A61B 5/103 600/534 |
| 2015/0190088 A1 | 7/2015 | Chen et al. | |
| 2016/0022204 A1* | 1/2016 | Mostov | A61B 5/0002 600/301 |
| 2016/0120434 A1* | 5/2016 | Park | A61B 5/4839 600/301 |
| 2018/0098701 A1* | 4/2018 | Blomqvist | A61B 5/02427 |
| 2018/0106897 A1* | 4/2018 | Shouldice | G01S 13/56 |

FOREIGN PATENT DOCUMENTS

| | | |
|---|---|---|
| KR | 10-2013-0063364 A | 6/2013 |
| KR | 10-2014-0039452 A | 4/2014 |
| KR | 10-2015-0094256 A | 8/2015 |
| KR | 10-2015-0134032 A | 12/2015 |
| KR | 10-1601895 B1 | 3/2016 |
| KR | 10-2016-0074062 A | 6/2016 |

* cited by examiner

METHOD FOR DETECTING ABNORMAL RESPIRATION USING A PHOTOPLETHYSMOGRAPHY (PPG) SIGNAL

CROSS-REFERENCE TO RELATED APPLICATION

This application claims priority to Korean Patent Application No. 10-2016-0135222 filed on Oct. 18, 2016 in the Korean Intellectual Property Office (KIPO), the entire content of which is hereby incorporated by reference.

BACKGROUND

1. Field of the Invention

The present disclosure relates to apparatus and method for detecting an abnormal respiration, and more particularly, to apparatus and method for detecting an apnea or abnormal respiration by using biological signals.

2. Description of Related Art

As the quality of life has increased, due to the increase in income, various self-health inspection techniques using mobile devices such as smart bands and smart pads have been increasing in recent years. Such the techniques are developing in forms of wearable devices for measuring various biological signals such as a pulse.

In particular, there is a growing demand for apnea detection technology using a wearable device that can monitor survival of elders who live alone, soldiers isolated in a military operation, or those isolated in disaster and accident sites.

Apnea may be classified into a central apnea, an obstructive apnea, and a mixed apnea. The central apnea is a neurological disorder that stops all respiration efforts in a brain acting as a respiratory center. The obstructive apnea is caused by repeated obstructions of respiration during sleep due to a closure of an upper respiratory tract, which causes decrease in blood oxygen saturation. The mixed apnea refers to simultaneous occurrence of the central apnea and the obstructive apnea.

Recently, various devices for measuring biological signals such as a user's pulse are being developed due to advancement of smart devices, but there is not enough technology for apnea detection using biological signals which can be utilized for application services such as self-diagnosis in a user's familiar environment.

Thus, it would be necessary to have an abnormal respiration or apnea detection technology using a wearable device that can effectively monitor the survival of elders who live alone, soldiers isolated in a military operation, soldiers, and those isolated in disaster and accident sites.

Also, interest in sleep quality has been increased considerably. Snoring and sleep apnea, which have the greatest effect on the sleep quality, cause fatigue in daily life due to insufficient supply of oxygen, resulting in decreased efficiency of learning and work, leading to the occurrence of industrial accidents and accidents such as traffic accidents, which can lead to cardiovascular and brain activity failure due to insufficient oxygen supply in the body.

Therefore, it is necessary to use the measured biological signal to provide an abnormal respiration or apnea detection technique that can provide application services such as low-cost sleep quality self-diagnosis and the like in the user's familiar environment.

SUMMARY

Accordingly, exemplary embodiments of the present disclosure are provided to substantially obviate one or more problems due to limitations and disadvantages of the related art.

Embodiments of the present disclosure provide an abnormal respiration detection apparatus for detecting an apnea or an abnormal respiration by using a biological signal.

Embodiments of the present disclosure also provide an abnormal respiration detection method.

Embodiments of the present disclosure also provide a computer-readable recording medium on which a computer program for performing the abnormal respiration detection method is recorded.

Technical objects of the present disclosure are not limited to the aforementioned technical objects and other technical objects which are not mentioned will be apparently appreciated by those skilled in the art from the following description.

In order to achieve the above-described objective, an aspect of the present disclosure provides an abnormal respiration detection apparatus comprising a sensor for sensing a photoplethysmography (PPG) signal from an optical signal reflected and received from a user's body; a band pass filter for extracting a signal of a required band from the PPG signal received from the sensor; an analog-to-digital converter for performing a digital conversion on the filtered PPG signal; and an abnormal respiration recognition unit deriving a respiration rate signal from the digital-converted PPG signal, deriving a plurality of respiration rate characteristic values through a time axis analysis on the derived respiration rate signal, and detecting an abnormal respiration using the derived plurality of respiration rate characteristic values.

The plurality of respiration rate characteristic values may include at least one of a peak-to-valley value and a number of peaks during a unit time in the respiration rate signal represented in a time axis.

The abnormal respiration recognition unit may determine the abnormal respiration by performing a first analysis using a peak-to-valley value and a second analysis using a number of peaks during a unit time in the respiration rate signal represented in a time axis.

The abnormal respiration recognition unit may perform the first analysis by comparing a difference between a maximum peak-to-valley value during a current unit time and a previously-calculated moving average of peak-to-valley values with a first reference value, and performs the second analysis by comparing a difference between a number of peaks during the current unit time and a previously-calculated moving average of a number of peaks during a unit time with a second reference value.

The abnormal respiration recognition unit may reflect the maximum peak-to-valley value during the current unit time to the moving average of peak-to-valley values when the difference between the maximum peak-to-valley value during the current unit time and the previously-calculated moving average of peak-to-valley values does not exceed the first reference value, and reflects the number of peaks during the current unit time to the moving average of the number of peaks when the difference between the number of peaks during the current unit time and the previously-calculated moving average of the number of peaks during a unit time does not exceeds the second reference value.

The abnormal respiration recognition unit may obtain the respiration rate signal by performing a band pass filtering of a respiratory frequency band of 0.2 to 0.3 Hz frequency on the sensed PPG signal.

The required band may be 0.1 to 1.2 Hz frequency band.

The abnormal respiration detection apparatus may be included in a wearable device worn on a user's wrist.

The abnormal respiration detection apparatus may further comprise a band rejection filter rejecting an unnecessary noise band from the PPG signal sensed through the sensor and outputting the filtered PPG signal to the band pass filter.

The abnormal respiration may include at least one of a central apnea, an obstructive apnea, and a mixed apnea.

The abnormal respiration detection apparatus may further comprise a result output display outputting a detection result on whether the abnormal respiration recognition unit recognizes the abnormal respiration; and a communication input/output interface transmitting the detection result.

In order to achieve the above-described objective, another aspect of the present disclosure provides an abnormal respiration detection method comprising sensing a photoplethysmography (PPG) signal from an optical signal reflected and received from a user's body; performing a band pass filtering for extracting a signal of a required band from the sensed PPG signal; performing a digital conversion on the filtered PPG signal; and deriving a respiration rate signal from the digital-converted PPG signal, deriving a plurality of respiration rate characteristic values through a time-axis analysis on the derived respiration rate signal, and detecting an abnormal respiration using the derived plurality of respiration rate characteristic values.

The plurality of respiration rate characteristic values may include at least one of a peak-to-valley value and a number of peaks during a unit time in the respiration rate signal represented in a time axis.

The detecting an abnormal respiration may further include performing a first analysis by comparing a difference between a maximum peak-to-valley value during a current unit time and a previously-calculated moving average of peak-to-valley values with a first reference value.

The detecting an abnormal respiration may further include performing a second analysis by comparing a difference between a number of peaks during the current unit time and a previously-calculated moving average of a number of peaks during a unit time with a second reference value.

The detecting an abnormal respiration may further include reflecting the maximum peak-to-valley value during the current unit time to the moving average of peak-to-valley values when the difference between the maximum peak-to-valley value during the current unit time and the previously-calculated moving average of peak-to-valley values does not exceed the first reference value.

The detecting an abnormal respiration may further include reflecting the number of peaks during the current unit time to the moving average of the number of peaks when the difference between the number of peaks during the current unit time and the previously-calculated moving average of the number of peaks during a unit time does not exceeds the second reference value.

The detecting an abnormal respiration may further include obtaining the respiration rate signal by performing a band pass filtering of a respiratory frequency band of 0.2 to 0.3 Hz frequency on the sensed PPG signal.

The abnormal respiration may include at least one of a central apnea, an obstructive apnea, and a mixed apnea.

According to the embodiments of the present disclosure as described above, it is made possible to provide a device and a method for abnormal respiration detection which can be used in a wearable device having a photoelectric element, so that people with difficulty in sleeping can self-diagnose sleep apnea symptoms, and the quality of life of the user can be improved.

Further, the embodiments of the present disclosure can be utilized to monitor the survival of elders who live alone, soldiers isolated in a military operation, persons isolated in disaster and accident sites, thereby contributing to public and social safety and building of welfare society and nation.

BRIEF DESCRIPTION OF DRAWINGS

Exemplary embodiments of the present disclosure will become more apparent by describing in detail exemplary embodiments of the present disclosure with reference to the accompanying drawings, in which.

DESCRIPTION OF EXEMPLARY EMBODIMENTS

Figure 1:
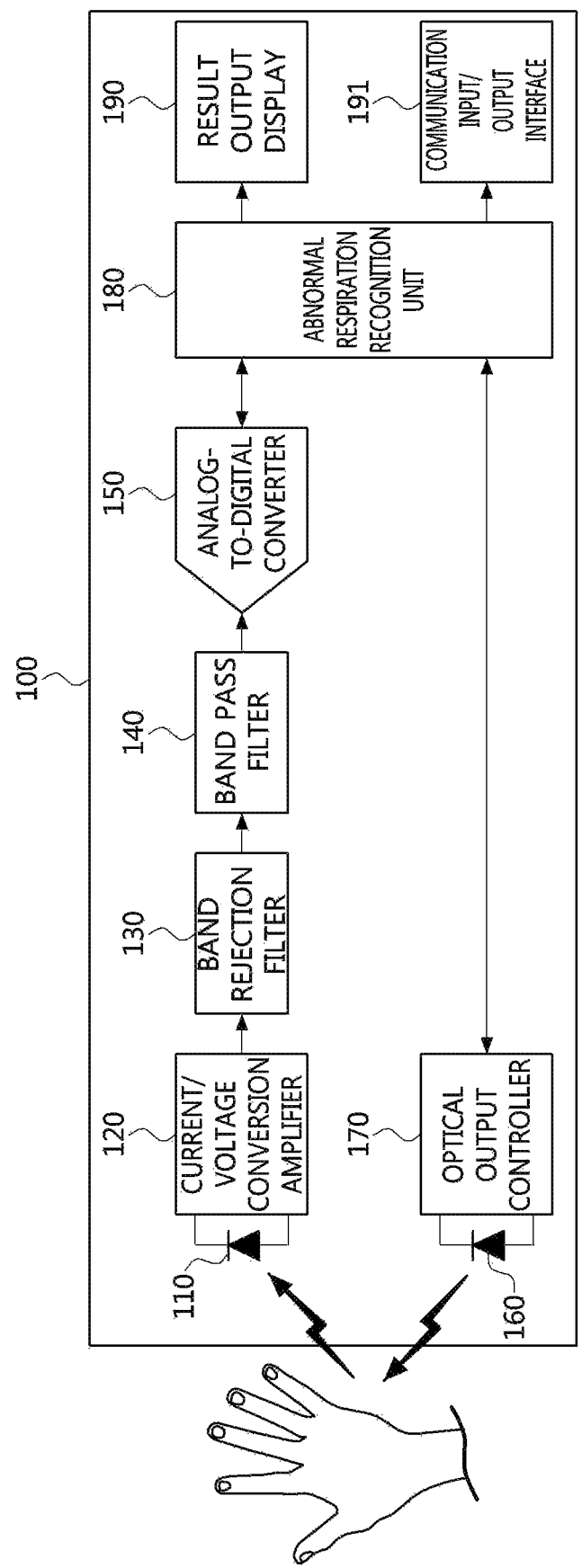
FIG. 1 is a block diagram illustrating an abnormal respiration detection apparatus according to an embodiment of the present disclosure.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Combinations of respective blocks in an accompanying block diagram and respective operations in a flowchart may be performed by application program instructions. These application program instructions can be mounted on a processor of a general purpose computer, a special purpose computer, or other programmable data processing equipment, and thus the instructions performed by the processor of the computer or other programmable data processing equipment generate a means for performing functions described in the respective blocks of the block diagram or the respective operations of the flowchart. To implement functions in a specific way, these application program instructions can be stored in a computer-usable or computer-readable memory capable of aiming for a computer or other programmable data processing equipment, so that the instructions stored in the computer-usable or computer-readable memory can also produce a manufactured item including an instruction means for performing functions described in the respective blocks of the block diagram or the respective operations of the flowchart.

In addition, each block or operation may indicate a part of a module, a segment or a code including one or more executable instructions for executing specific logical function(s). It should be noted that mentioned functions described in blocks or operations can be executed out of order in some alternative embodiments. For example, two consecutively shown blocks or operations can be performed substantially at the same time, or can be performed in a reverse order according to the corresponding functions.

Hereinafter, exemplary embodiments according to the present disclosure will be described in detail by referring to accompanying drawings. However, the exemplary embodiments according to the present disclosure may be changed into various forms, and thus the scope of the present disclosure is not limited to the exemplary embodiments which will be described. The exemplary embodiments are provided to assist the one of ordinary skill in the art in gaining a comprehensive understanding of the methods, apparatuses, and/or systems described herein.

Hereinafter, preferred embodiments according to the present disclosure will be described in detail with reference to the accompanying drawings.

FIG. 1 is a block diagram illustrating an abnormal respiration detection apparatus according to an embodiment of the present disclosure.

The abnormal respiration detection apparatus 100 according to the present disclosure may be implemented in a wearable device having photoelectric elements, for example, a smart band, a smart watch, or the like.

When the wearable device including the abnormal respiration detection apparatus according to the present disclosure is worn by a user, photoplethysmography (PPG) signal may be detected through photoelectric elements 110 and 160, and the detected PPG signal may be analyzed by an abnormal respiration recognition unit 180 (e.g., abnormal respiration awareness module or an abnormal respiration awareness engine) in a microcontroller provided in the wearable device. Accordingly, the user's abnormal respiration may be detected.

The PPG signal is a signal that measures changes in the blood component density (hemoglobin, etc.) in blood vessels according to heartbeats, using light absorption, reflection, and scattering. The PPG signal may be sensed by measuring a blood flow using an absorption rate of a light absorbed or reflected by tissues, when irradiating the light to a specific region (e.g., a wrist) of a human body. When the light is irradiated on the human body, the transmission degree of light is changed by the density change of the blood. Since the amount of change is due to the blood flow, the PPG signal may be measured using this phenomenon.

In the present disclosure, the abnormal respiration may include the obstructive apnea, the central apnea, the mixed apnea, and the like, and may also include other abnormal respirations of various symptoms.

The abnormal respiration detection apparatus 100 according to an embodiment of the present disclosure may comprise PPG sensors 110 and 160 for measuring the PPG of the user, a voltage/current conversion amplifier 120, a band rejection filter 130, a band pass filter 140, an analog-to-digital converter (ADC) 150, and an optical output controller 170.

The PPG sensor may include a light emitting element 160 and a light receiving element 110. The light emitting element 160 may be a light emitting diode (LED), and the light receiving element 110 may be a light receiving diode. The light emitting diode may generate a light having a band of a certain wavelength, and examples of the wavelengths to be generated may include 535 nm, 660 nm, and 940 nm.

The abnormal respiration detection apparatus 100 may further comprise a light emitting diode driver for operation and control of the PPG sensor.

Meanwhile, the optical output controller 170 may control the light amount of the light emitting diode 160, and may have a form of a digital-to-analog converter (DAC).

The light emitted from the light emitting element 160 and reflected at a wrist of the user may be received through the light receiving element 110 and may be output in a form of a current and converted into a voltage signal through the current/voltage converter 120.

The signal outputted from the current/voltage converter 120 is processed by the band rejection filter 130, the band pass filter 140, and the analog-to-digital converter (ADC) 150, and transmitted to the abnormal respiration recognition unit 180.

The band rejection filter 130 may remove 50 Hz or 60 Hz power frequency signals from an input signal (i.e., the PPG signal output from the current/voltage converter), and the band pass filter 140 may filter 0.1 Hz to 1.2 Hz signal including an adult pulse of approximately 50 beats per minute (BPM) to 100 BPM from an input signal (i.e., the PPG signal output from the band rejection filter). The band-pass filtered signal may be converted to a digital signal via the ADC 150.

The PPG signal converted into the digital signal may be transmitted to the abnormal respiration recognition unit 180 and an abnormal respiration detection according to the present disclosure may be performed on the transmitted PPG signal.

The abnormal respiration recognition unit 180 may calculate a respiration rate from the sensed PPG signal and perform an apnea detection algorithm according to the present disclosure. The apnea detection algorithm according to the present disclosure is based on a time axis analysis and is a two-step analysis.

The abnormal respiration recognition unit 180 according to the present disclosure may be implemented in a form of an engine or a module, and may be included in a microcontroller of the wearable device.

The recognition result obtained through the abnormal respiration recognition unit 180 may be transferred to a recognition result output unit, and the recognition result output unit may be implemented in a form of a result output display 190 and a communication input/output interface 191.

The result output display 190 may display the recognition result on the user's respiration on a screen and provide the result to the user, and the communication input/output interface 191 may transmit the recognition result to a separate controller located remotely or near to the user.

The abnormal respiration detection apparatus according to the present disclosure, which may include a configuration as illustrated in FIG. 1, may detect an abnormal respiration of the user by extracting a respiration rate signal (e.g., respiration intensity induced variability (RIIV) signal) from a PPG signal of a wrist of the user. The embodiments of the present disclosure can be effectively used to detect a user's apnea, particularly when monitoring is needed for reasons of disaster, health or medical care.

Figure 2:
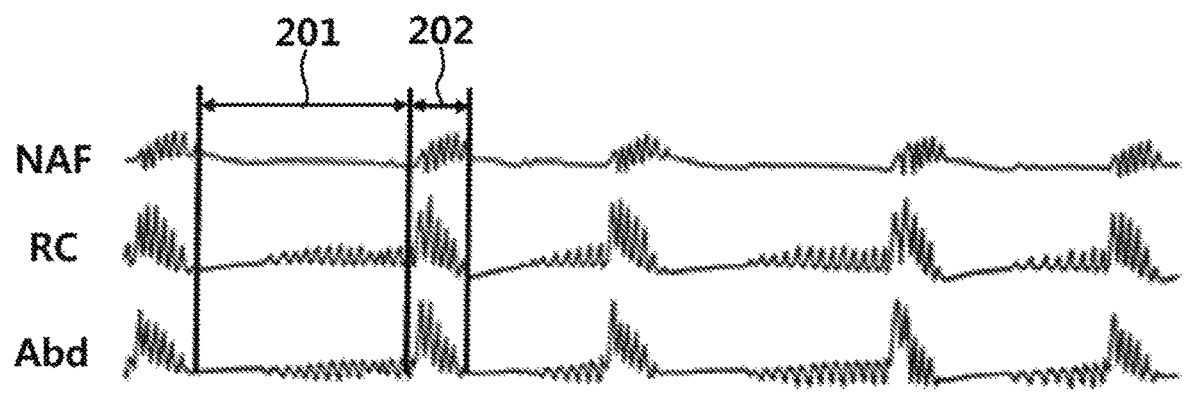
FIG. 2 is a biological signal response graph of an obstructive apnea which is one of abnormal respirations.

FIG. 2 is a biological signal response graph of an obstructive apnea which is one of abnormal respirations.

As described above, the obstructive apnea is one of various abnormal respirations that can be detected by the abnormal respiration detection apparatus according to the present disclosure.

An obstructive sleep apnea (OSA) is an apnea occurring when a respiratory tract is obstructed as muscles relax during sleep, and is a more common symptom than a central sleep apnea (CSA) occurring when a diaphragm itself does not exercise and respiration is interrupted.

During sleep, the muscles of the body usually become relaxed, and the respiratory tract droops, causing the sleep apnea during sleep. Although many people experience temporary or intermittent symptoms of obstructive sleep apnea, fewer people experience severe chronic obstructive sleep apnea.

Referring to FIG. 2, a first period 201 and a second period 202 are repeated, and signal characteristics of NAF, RC, and Abd in the first period 201, which is an abnormal respiration or apnea period, are different from those signal characteristics in the second period 202, which is a normal respiration period.

Here, the NAF signal represents a nasal air flow, the RC signal represents a thoracic cavity (or, rib cage) respiratory movement, and the Abd signal represents an abdominal respiratory movement.

In the first period 201 of the abnormal respiration period, respiratory movements of chest and abdomen occur due to respiratory movement signals of a brainstem respiratory center, but it is understood that air flow of the nasal cavity is blocked. That is, in the obstructive apnea, the air flow in the nasal cavity is blocked although there is respiration effort in the chest and abdomen.

Figure 3:
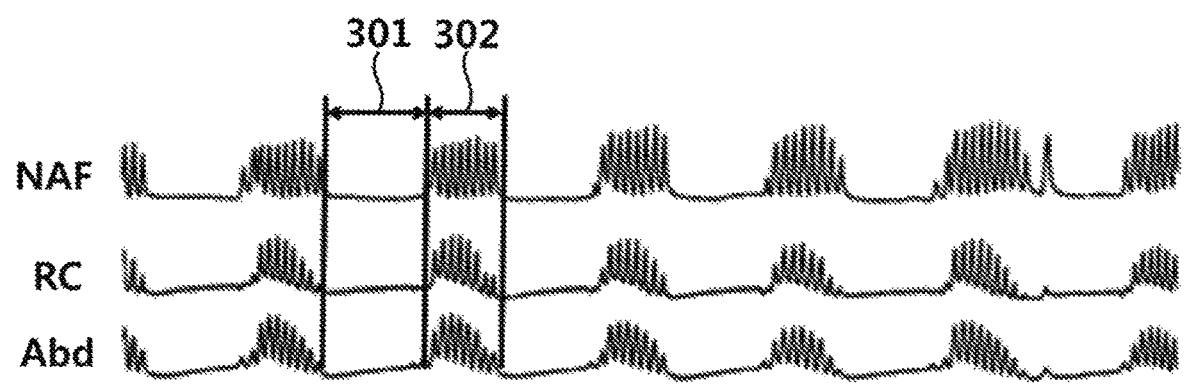
FIG. 3 is a biological signal response graph of a central apnea which is one of abnormal respirations.

FIG. 3 is a biological signal response graph of a central apnea which is one of abnormal respirations.

In the graph illustrated in FIG. 3 showing biological signals of the central apnea, a first period 301 which is a normal respiration period and a second period 302 which is an abnormal respiration period are repeated at regular intervals.

In the biological signal response graph according to the central apnea illustrated in FIG. 3, it can be seen that there are not air flow of the nasal cavity and the respiratory movements of the thoracic cavity and abdominal cavity due to non-occurrence of respiratory movement signals of the brainstem respiratory center. That is, in the central apnea, there are no respiration efforts.

The abnormal respirations illustrated in FIGS. 2 and 3 are merely examples of abnormal respirations to be detected in the present disclosure, and a range of abnormal respirations to be sensed by embodiments of the present disclosure is not limited thereto.

Figure 4:
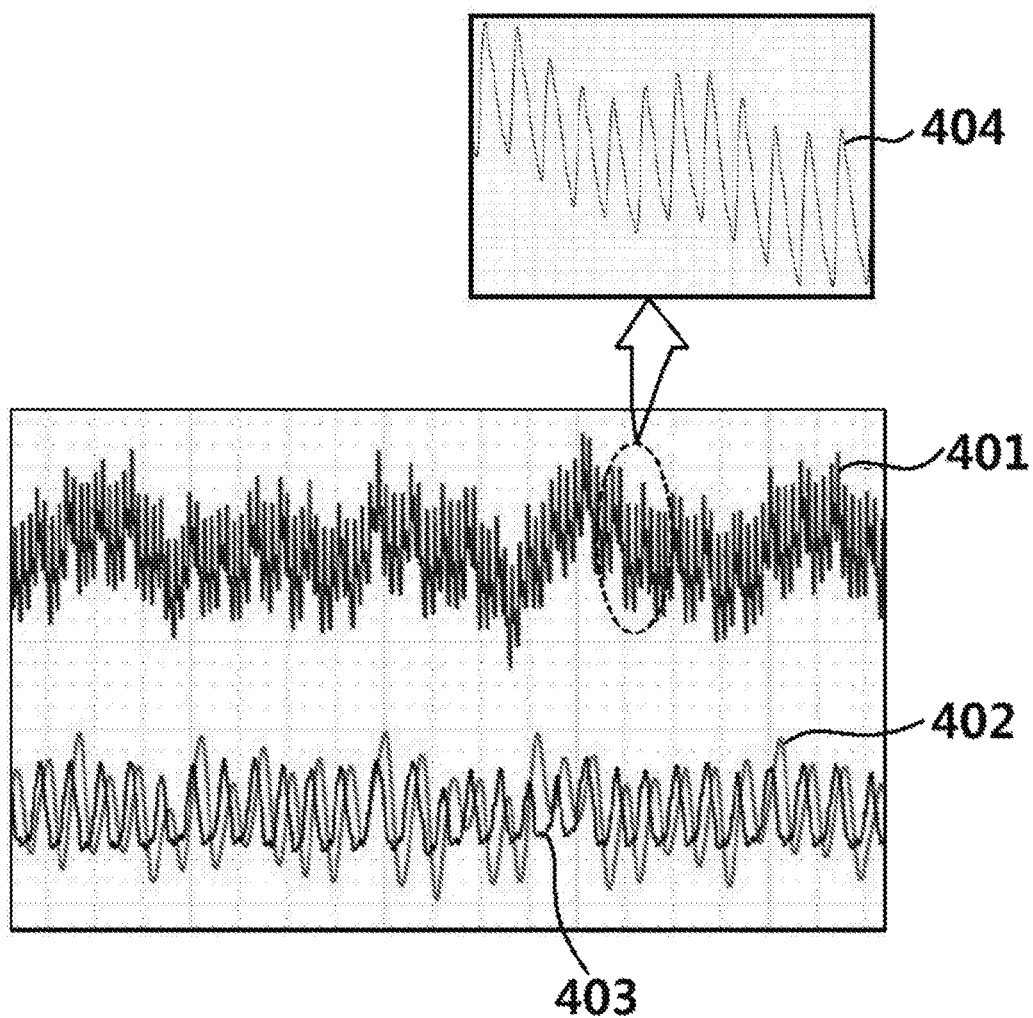
FIG. 4 illustrates a PPG signal and a respiratory signal measured using a commercial respiration measurement system.

FIG. 4 illustrates a PPG signal and a respiratory signal measured using a commercial respiration measurement system.

Referring to FIG. 4, a PPG signal 401 which is actually measured from a human, a respiratory signal 403 measured using a commercial respiration measurement system (e.g., MP150 or RSP100C of BIOPAC systems Inc.) which directly measures respiratory movements of a chest of the human, and a respiration rate signal 402 calculated using the sensed PPG signal are illustrated. It can be seen that the actually measured respiratory signal 403 and the calculated respiration rate signal 402 are synchronized with very similar periods.

Figure 5:
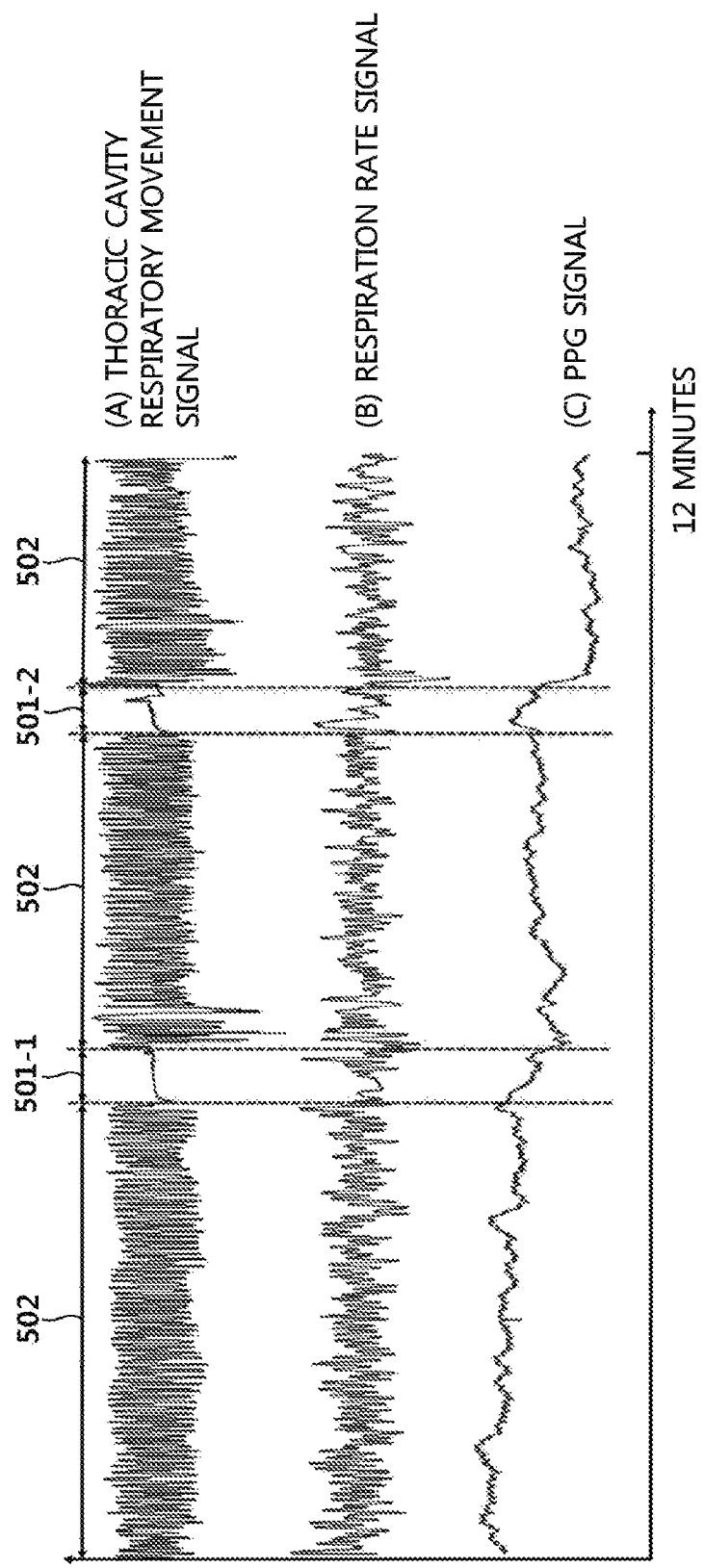
FIG. 5 is a graph in which a thoracic cavity respiratory movement signal, a respiration rate signal, and a PPG signal are compared in a time axis.

FIG. 5 is a graph in which a thoracic cavity respiratory movement signal, a respiration rate signal, and a PPG signal are compared in a time axis.

The thoracic cavity respiratory movement signal (denoted as (a)) shown in FIG. 5 is a signal actually measured using a commercial respiration measurement system (e.g., MP150 or RSP100C of BIOPAC Systems Inc.) during 12 minutes.

The PPG signal (denoted as (c)) is a signal output from the PPG sensor 110 according to an embodiment of the present disclosure, and the respiration rate signal (denoted as (b)) represents a respiration rate signal calculated according to the present disclosure.

Referring to the graph of FIG. 5, normal respiration periods 502 show a respiration rate signal having a regular period and peak-to-valley values. On the other hand, the thoracic cavity respiratory movement signal (a) and the respiration rate signal (b) in abnormal respiration periods 501-1 and 501-2 (e.g., apnea periods in which the obstructive apnea occurs) show that the periods and peak-to-valley values are very irregular as compared to the respiratory movement signal and the respiration rate signal calculated during the normal respiration periods 502.

In an embodiment of the present disclosure, abnormal respiration such as apnea may be detected by analyzing signal characteristics of the abnormal respiration periods in which the irregularity degree of the periods and peak-to-valley values becomes larger than the normal respiration period.

In an embodiment of the present disclosure, a two-step analysis may be performed on the respiration rate signal in the time axis to detect the abnormal respiration.

Figure 6:
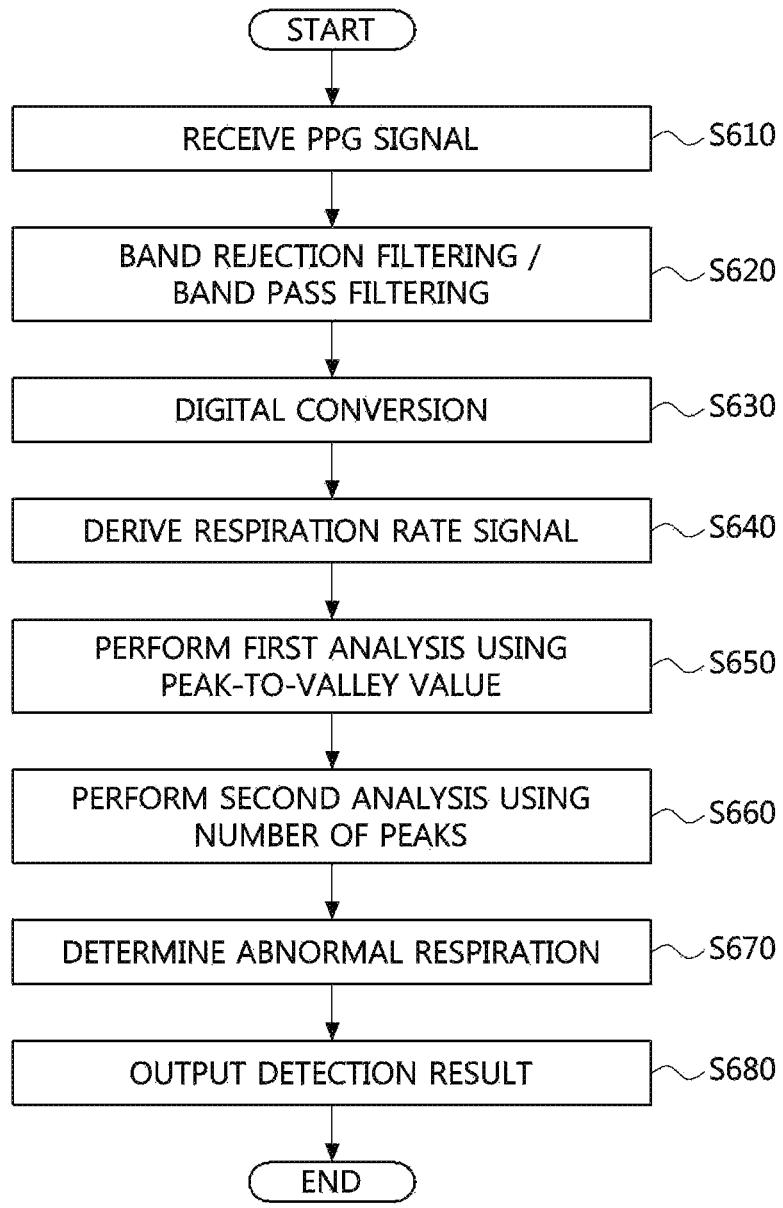
FIG. 6 is a schematic flowchart of an abnormal respiration detection method according to an embodiment of the present disclosure.

FIG. 6 is a schematic flowchart of an abnormal respiration detection method according to an embodiment of the present disclosure.

Referring to FIG. 6, in an abnormal respiration detection method according to an embodiment of the present disclosure, a PPG signal may be received through a wearable device worn on a wrist, etc. (S610), a noise signal may be removed from the received PPG signal by performing a band rejection filtering and a band pass filtering on the received PPG signal (S620), and a digital conversion may be performed on the processed PPG signal (S630).

The band rejection filtering may remove 50 Hz or 60 Hz power frequency signals from an input signal and only 0.1 Hz to 1.2 Hz signal corresponding to the adult pulse of approximately 50 BPM to 100 BPM may be passed through the band pass filtering.

For the converted digital signal, a respiration rate signal may be derived through a band pass filtering that filters only the respiration frequency component band (S640).

Here, the respiration rate signal may be derived from the sensed PPG signal. That is, the respiration rate signal may be derived by performing a band pass filtering of 0.2 Hz (12 times per minute) to 0.3 Hz (18 times per minute) signal which is a respiratory frequency component from the pre-processed and digitally converted PPG signal.

For the derived respiration rate signal, a first analysis and a second analysis according to the present disclosure may be performed in a time axis (S650, S660). The first analysis may be performed based on peak-to-valley values, and the second analysis may be performed based on the number of peaks during a unit time.

When an abnormal respiration is detected (S670), the detection result may be output (S680). Herein, an abnormal respiration may include an obstructive apnea, a central apnea, a mixed apnea, and the like, and may include other abnormal respirations of various symptoms. Also, the output of the detection result may be displayed in a form of displaying on a screen or in a form of being transmitted to a separate control device located at a long distance or a short distance.

Figure 7:
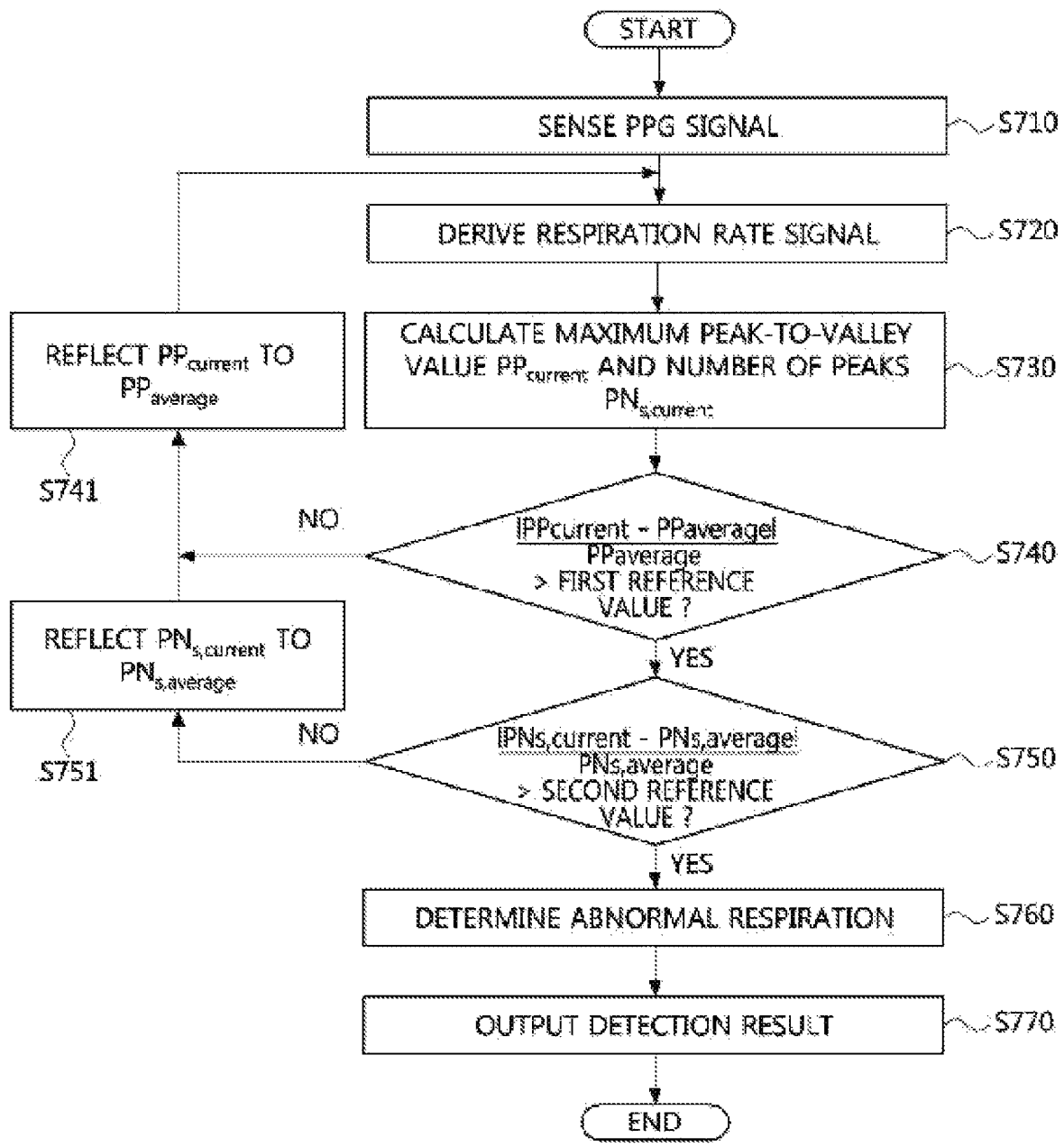
FIG. 7 is a detailed operation sequence chart illustrating an abnormal respiration detection method using a two-step time axis analysis according to an embodiment of the present disclosure.

FIG. 7 is a detailed operation sequence chart illustrating an abnormal respiration detection method using a two-step time axis analysis according to an embodiment of the present disclosure.

For the abnormal respiration detection according to an embodiment of the present disclosure, a step S710 of sensing a PPG signal of a user which is inputted in real time and a step S720 of deriving a respiration rate signal may be performed. Here, the step S710 of sensing the PPG signal may be a step including the step S610 of receiving a PPG signal, the step S620 of band rejection filtering and band pass filtering, and the step S630 of digital conversion which are illustrated in FIG. 6.

Also, the step S720 of deriving the respiration rate signal may be configured identically to the step S640 of deriving the respiration rate signal which was explained referring to FIG. 6.

For the derived respiration rate signal, the two-step analysis according to the present disclosure may be performed. First, for a predetermined time period (i.e., for a predetermined unit time), a maximum peak-to-valley value $PP_{current}$ and the number of peaks $PN_{s,current}$ may be calculated (S730).

Thereafter, the first analysis according to the present disclosure may be performed using a difference between the maximum peak-to-valley value calculated during the current unit time and a previously-calculated moving average of peak-to-valley values (S740). Here, the difference between the maximum peak-to-valley value calculated during the current unit time and the previously-calculated moving average of peak-to-valley values ma be substituted with a ratio of the difference between the maximum peak-to-valley value calculated during the current unit time and the moving average of peak-to-valley values to the moving average of peak-to-valley values. In this case, the first analysis according to the abnormal respiration detection according to the present disclosure may be represented as below Equation $$\begin{cases} \frac{|PPcurrent - PPaverage|}{PPaverage} > 10\%, & \text{first detection of apnea} \\ \frac{|PPcurrent - PPaverage|}{PPaverage} \leq 10\%, & \text{normal respiration} \end{cases} \quad \text{[Equation 1]}$$

In Equation 1, $PP_{current}$ may represent the maximum peak-to-valley value during the current unit time, and $PP_{average}$ may represent the previously-calculated moving average of peak-to-valley values. Also, the first reference value is 10%.

Herein, the moving average of peak-to-valley values is a pre-stored value, and it may be obtained by repeating the steps 710, 720, and 730 several times before the analysis is performed and averaging the values obtained through the repetitions.

If a difference between the current maximum peak-to-valley value and the previously-calculated moving average of peak-to-valley values is less than or equal to the first reference value (i.e., 'NO' in S740), it may be determined that the abnormal respiration is not detected, and the moving average of peak-to-valley values may be updated by reflecting the current maximum peak-to-valley value to the moving average of peak-to-valley values (S741).

On the other hand, if the difference between the current maximum peak-to-valley value and the previously stored moving average of peak-to-valley values exceeds the first reference value (i.e., 'YES' in S740), it may be first classified as an abnormal respiration candidate, and the second analysis may be further performed for more reliable abnormal respiration detection (S750).

The second analysis may be performed by comparing the number of peaks during a unit time with a previously-calculated moving average of the number of peaks. More specifically, the second analysis may be performed by comparing a difference between the number of peaks during the current unit time and a previously-calculated moving average the number of peaks during a unit time pith a second reference value. Here, the difference between the number of peaks during the current unit time and the moving average value of the number of peaks during a unit time may be substituted with a ratio of the difference between the number of peaks during the current unit time and the moving average of the number of peaks during a unit time to the moving average of the number of peaks during a unit time. In this case, the second analysis according to the present disclosure may be represented as below Equation 2.

$$\begin{cases} \frac{|PNs, current - PNs, average|}{PNs, average} > 40\%, & \text{second detection of apnea} \\ \frac{|PNs, current - PNs, average|}{PNs, average} \leq 40\%, & \text{normal respiration} \end{cases} \quad \text{[Equation 2]}$$

In Equation 2, $PN_{s,current}$ may represent the number of peaks during the current unit time, and $PN_{s,average}$ may represent the moving average of the number of peaks during a unit time which has been previously calculated through several unit times. Also, the second reference value is 40%.

In the second analysis according to the present disclosure, if a ratio of the difference between the number of peaks during the current unit time and the moving average of the number of peaks to the moving average of the number of peaks is less than or equal to the second reference value (e.g., 40%), it may be determined as a normal respiration. On the other hand, if the ratio exceeds the second reference value (e.g., 40%), it may be determined as abnormal respiration (S760).

As a result of the second analysis, if the normal respiration is determined (i.e., 'NO' in S750), the number of peaks during the current unit time may reflected to the moving average of the number of peaks. That is, a new moving average to which the number of peaks during the current unit time is reflected may be calculated and stored (S751).

If the abnormal respiration is determined, the determined detection result may be displayed through the result output display 190 or transmitted to a separate control unit or control apparatus through the communication input/output interface 191 (S770).

The methods according to embodiments of the present disclosure may be implemented as program instructions executable by a variety of computers and recorded on a computer readable medium. The computer readable medium may include a program instruction, a data file, a data structure, or a combination thereof. The program instructions recorded on the computer readable medium may be designed and configured specifically for the present disclosure or can be publicly known and available to those who are skilled in the field of computer software.

Also, examples of the computer readable medium may include a hardware device such as ROM, RAM, and flash memory, which are specifically configured to store and execute the program instructions. Examples of the program instructions include machine codes made by, for example, a compiler, as well as high-level language codes executable by a computer, using an interpreter.

While some aspects of the present disclosure have been described in the context of an apparatus, it may also represent a description according to a corresponding method, wherein the block or apparatus corresponds to a feature of the method step or method step. Similarly, aspects described in the context of a method may also be represented by features of the corresponding block or item or corresponding device. Some or all of the method steps may be performed by (or using) a hardware device such as, for example, a microprocessor, a programmable computer, or an electronic circuit. In some embodiments, one or more of the most important method steps may be performed by such an apparatus.

In embodiments of the present disclosure, a programmable logic device (e.g., a field programmable gate array (FPGA)) may be used to perform some or all of the functions of the methods described herein. In embodiments, the FPGA may operate in conjunction with a microprocessor to perform one of the methods described herein. Generally, the methods are preferably performed by some hardware device.

While the embodiments of the present disclosure and their advantages have been described in detail above, it should be understood that various changes, substitutions and alterations may be made herein without departing from the scope of the disclosure.

What is claimed is:

1. An abnormal respiration detection method comprising:
sensing a photoplethysmography (PPG) signal from an optical signal reflected and received from a user's body;
performing a band pass filtering for extracting a signal of a required band from the sensed PPG signal;
performing a digital conversion on the filtered PPG signal; and
deriving a respiration rate signal from the digital-converted PPG signal, deriving a plurality of respiration rate characteristic values through a time-axis analysis on the derived respiration rate signal, and detecting an abnormal respiration using the derived plurality of respiration rate characteristic values,
wherein the plurality of respiration rate characteristic values include peak-to-valley values of the respiration rate signal expressed on the time axis and the number of peaks per unit time of the respiration rate signal,
wherein the detecting an abnormal respiration is performed by a first analysis using the peak-to-valley values of the respiration rate signal and then a second analysis using the number of peaks per unit time of the respiration rate signal, the second analysis being successively performed if the first analysis indicates the detection of abnormal respiration,
wherein the first analysis is performed according to Equation 1 by comparing a difference between a maximum peak-to-valley value of the peak-to-valley values during a current unit time and a previously-calculated moving average of the peak-to-valley values during a previous unit time with a first reference value, $$\begin{cases} \frac{|PPcurrent - PPaverage|}{PPaverage} > 10\%, & \text{first detection of apnea} \\ \frac{|PPcurrent - PPaverage|}{PPaverage} \le 10\%, & \text{normal respiration} \end{cases} \quad \text{[Equation 1]}$$

where $PP_{current}$ represents the maximum peak-to-valley value during the current unit time, and $PP_{average}$ represents the previously-calculated moving average of the peak-to-valley values, and wherein the second analysis is performed according to Equation 2 by comparing a difference between the number of peaks during the current unit time and a previously-calculated moving average value of the number of peaks during the previous unit time with a second reference value, $$\begin{cases} \frac{|PNs, current - PNs, average|}{PNs, average} > 40\%, & \text{second detection of apnea} \\ \frac{|PNs, current - PNs, average|}{PNs, average} \le 40\%, & \text{normal respiration} \end{cases} \quad \text{[Equation 2]}$$

where $PN_{current}$ represents the number of peaks during the current unit time, and $PN_{average}$ represents the moving average of the number of peaks during the previous unit time which has been previously calculated through several unit times,
wherein the detecting an abnormal respiration further includes adding the maximum peak-to-valley value during the current unit time to the moving average of peak-to-valley to recalculate an updated moving average of peak-to-valley values, when the difference between the maximum peak-to-valley value during the current unit time and the previously-calculated moving average of peak-to-valley values does not exceed the first reference value, and
wherein the detecting an abnormal respiration further includes adding the number of peaks during the current unit time to the moving average of the number of peaks to recalculate an updated moving average of the number of peaks, when the difference between the number of peaks during the current unit time and the previously-calculated moving average of the number of peaks during a unit time does not exceed the second reference value.

2. The abnormal respiration detection method according to claim 1, wherein the detecting an abnormal respiration further includes obtaining the respiration rate signal by performing a band pass filtering of a respiratory frequency band of 0.2 to 0.3 Hz frequency on the sensed PPG signal.

3. The abnormal respiration detection method according to claim 1, wherein the abnormal respiration includes at least one of a central apnea, an obstructive apnea, and a mixed apnea.

* * * * *